United States Patent
Diaz-Fernandez et al.

(10) Patent No.: US 7,964,603 B2
(45) Date of Patent: Jun. 21, 2011

(54) SUBSTITUTED TETRAHYDRO-QUINOLINE-SULFONAMIDE COMPOUNDS, THEIR PREPARATION AND USE AS MEDICAMENTS

(75) Inventors: Jose Luis Diaz-Fernandez, Barcelona (ES); Ramon Merce-Vidal, Barcelona (ES); Lajos Novak, Budapest (HU)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 179 days.

(21) Appl. No.: 12/175,660

(22) Filed: Jul. 18, 2008

(65) Prior Publication Data

US 2009/0030013 A1 Jan. 29, 2009

(30) Foreign Application Priority Data

Jul. 19, 2007 (EP) ..................................... 07380216

(51) Int. Cl.
*A61K 31/496* (2006.01)
*C07D 215/58* (2006.01)

(52) U.S. Cl. .................................. 514/253.06; 544/363
(58) Field of Classification Search ........................ None
See application file for complete search history.

(56) References Cited

U.S. PATENT DOCUMENTS

| | | | |
|---|---|---|---|
| 6,423,717 B1 * | 7/2002 | Bromidge et al. ....... | 514/252.13 |
| 6,727,270 B2 | 4/2004 | Kelly et al. | |
| 6,737,426 B1 | 5/2004 | Gericke et al. | |
| 6,770,642 B2 | 8/2004 | Cole et al. | |
| 7,144,883 B2 | 12/2006 | Caldirola et al. | |
| 7,572,787 B2 | 8/2009 | Caldirola et al. | |
| 7,655,690 B2 | 2/2010 | Merce Vidal et al. | |

FOREIGN PATENT DOCUMENTS

| | | |
|---|---|---|
| WO | WO 96/02537 | 2/1996 |
| WO | WO 96/11929 | 4/1996 |
| WO | WO 96/23783 | 8/1996 |
| WO | WO 97/08167 | 3/1997 |
| WO | WO2004/078176 | 9/2004 |
| WO | WO2005/014552 | 2/2005 |
| WO | WO2006/053785 | 11/2005 |
| WO | WO2007/025798 | 3/2007 |
| WO | WO2007/032572 | 3/2007 |

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Vippagunta et al. Advanced Drug Delivery Reviews, vol. 48, p. 3-26 (2001).*
Robichaud et al. In Annual Reports in Medicinal Chemistry, vol. 36, p. 11-20 (2000).*
Robichaud et al. In Annual Reports in Medicinal Chemistry, vol. 36, p. 11-20 (2000).*
Rogers et al. Psychopharmacology, vol. 158, p. 114-119 (2001).*
Bromidge et al. Bioorganic & Medicinal Chemistry Letters, vol. 11, p. 55-58 (2001).*
Tariska et al. Orv. Hetil, vol. 141(22), pp. 1189-1193 (2000) (Abstract provided).*
Bourson, et al, "Involvement of 5-HT$_6$ receptors in nigro-striatal function in rodents" *Brit. J. Pharmacology* (1998) 125: 1562-1566.
Bourson, et al, "Determination of the Role of the 5-ht$_6$ Receptor in the Rat Brain: A Study using Antsense Oligonucleotides" *J. Pharmacol. Exp. Ther.* (1996) 274(1): 173-180.
Bradbury, et al., "Muscarinic Receptor Binding and Activation of Second Messengers by Substituted N-Methyl-N-[4-(1-azacycloalkyl)-2-butynyl]acetamides" *J. Med. Chem.* (1991) 34: 1073-1079.
Branchek, et al., "5-HT$_6$ Receptors as Emerging Targets for Drug Discovery", *Annu. Rev. Pharmacol. Toxlcol.* (2000) 40: 319-334.
Choi, et al., "A Facile Debromination Reaction: Can Bromide Now Be Used as a Protective Group in Aromatic Systems?" *J. Am. Chem. Soc.* (2001) 123: 9202-9203.
Fix, Joseph, "Oral Drug Delivery, Small Intestine & Colon" *Encyclopedia of Controlled Drug Delivery*, vol. 2, Mathiowitz, E. (Ed.), John Wiley & Sons, Inc., New York (1999) 698-728.
Gilbert, Everett E., "Recent Developments in Preparative Sulfonation and Sulfation", *Synthesis* (Sep. 1969) 1: 3-10.
Hoyer D. and Martin, G., "5-HT$_6$ Receptor Classification and Nomenclature: Towards a Harmonization with the Human Genome" *Neuropharmacology* (1997) 36(4/5): 419-428. Kajigaeshi, et al., "Halogenation Using Quaternary Ammonium Polyhalides. XI.[1]) Bromination of Acetanilides by Use of Tetraalkylammonium Polyhalides" *Chem. Soc. Of Japan* (Jul. 1988) 61: 2681-2683.
Kohen, et al., "Cloning, Characterization, and Chromosomal Localization of a Human 5-HT$_6$ Serotonin Receptor" *J. of Neurochemistry* (1996) 66(1): 47-56.
Monsma, et al., "Cloning and Expression of a Novel Serotonin Receptor with High Affinity for Tricyclic Psychotropic Drugs" *Molecular Pharmacology* (1993) 43: 320-327.
Munson, Peter J., and Rodbard, D., "Ligand: A Versatile Computerized Approach for Characterization of Ligand-Binding Systems" *Analytical Biochemistry* (1980) 107: 220-239.

(Continued)

*Primary Examiner* — Emily Bernhardt
(74) *Attorney, Agent, or Firm* — Nobbe Martens Olson & Bear LLP

(57) ABSTRACT

The present invention refers to substituted tetrahydro-quinoline-sulfonamide compounds of general formula (I):

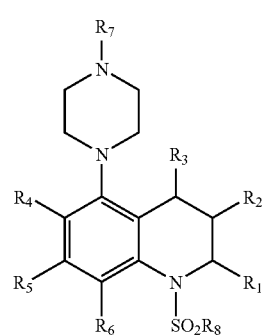

(I)

a method for their preparation, a medicament comprising these compounds and the use of substituted tetrahydro-quinoline-sulfonamide compounds for the preparation of medicaments for 5-HT$_6$ receptor regulation as well as for the treatment of disorders related thereto.

10 Claims, No Drawings

OTHER PUBLICATIONS

Nose, A. and Kudo, T., "Reduction of Heterocyclic Compounds. II.[1] Reduction of Heterocyclic Compounds with Sodium Borohydride-Transition Metal Salt Systems" *Chem. Pharm. Bull.* (1984) 32(6): 2421-2425.

Rogers, et al., "Cognitive Enhancement Effects of the Selective 5-$HT_6$ Antagonist SB-271046" *Br. J. Pharmacol. Suppl.* (1999) 127: 22.

Roth, et al., "Binding of Typical and Atypical Antipsychotic Agents to 5-Hydroxytryptamine-6 and 5-Hydroxytryptamine-7 Receptors" *J. Pharmacol. Exp. Ther.* (1994) 268: 1403-1410.

Routledge, et al., "Characterization of SB-271046: A potent, selective and orally active 5-$HT_6$ receptor antagonist" *Br. J. Pharm.* (2000) 130: 1606-1612.

Ruat, et al, "A Novel Rat Serotonin (5-$HT_6$) Receptor: Molecular Cloning Localization and Stimulation of cAMP Accumulation" *Biochemical and Biophysical Research Communications* (1993) 193(1): 268-276.

Sarvari, M.H., and Sharghi, H., "Zinc oxide (ZnO) as a new, highly efficient, and reusable catalyst for acylation of alcohols, phenols and amines under solvent free conditions" *Tetrahedron* (2005) 61: 10903-10907.

Sleight, et al., "Effects of altered 5-$ht_6$ expression in the rat: functional studies using antisense oligonucleotids" *Behavioural Brain Research* (1996) 73: 245-248.

Smid, et al., "Synthesis, Structure—Activity Relationships, and Biological Properties of 1-Heteroaryl-4-[ω-(1H-indol-3-yl)alkyl]piperazines, Novel Potential Antipsychotics Combining Potent Dopamine $D_2$ Receptor Antagonism with Potent Serotonin Reuptake Inhibition" *J. Med. Chem.* (2005) 48: 6855-6869.

Takada, K. and Yoshikawa, H., "Oral Drug Delivery", vol. 2, Mathiowitz, E. (Ed.), John Wiley & Sons, Inc., New York (1999) 728-742.

Woolley, et al., "A role for 5-$ht_6$ receptors in retention of spatial learning in the Morris water maze" *Neurophamacology* (2001) 41: 210-219.

Yoshioka, et al, "Central Distribution and Function of 5-$ht_6$ Receptor Subtype in the Rat Brain" *Ann. NY Acad. Sci.* (1998) 861: 244.

European Search Report, dated Nov. 16, 2007, issued in European Patent Application No. EP 07 38 0216.

Caldirola, Patrizia, "5-$HT_6$ Receptor Antagonism: A Novel Mechanism for the Management of Obesity" Power Point presentation at *Obesity and Related Disorders Conference*, The Hatton, Feb. 17, 2003, (pp. 1-25).

Da Silva Costa, et al, "Selective 5-$HT_6$ Receptor Blockade Improves Spatial Recognition Memory and Reverses Age-Related Deficits in Spatial Recognition Memory in the Mouse" *Neuropsychopharmacology* (2008) pp. 1-12.

Fisas, et al., "Chronic 5-$HT_6$ receptor modulation by E-6837 induces hypophagia and sustained weight loss in diet-induced obese rats" *Brit. J. Pharmacology* (2006) 148: 973-983.

Foley, et al., "The 5-$HT_6$ Receptor Antagonist SB-271046 Reverses Scopolamine-Disrupted Consolidation of a Passive Avoidance Task and Ameliorates Spatial Task Deficits in Aged Rats" *Neuropsychopharmacology* (2004) 29: 93-100.

Foley, et al., "The selective 5-$HT_6$ receptor antagonists SB-271046 and SB-399885 potentiate NCAM PSA immunolabeling of dentate granule cells, but not neurogenesis, in the hippocampal formation of mature Wistar rats" *Neuopharmacology* (2008) 54: 1165-1174.

Fone, Kevin C.F., "An update on the of the 5-hydroxytrptamine$_6$ receptor in cognitive function" *Neuropharmacology* (2008) 55: 1015-1022.

Greene, T.W. and Wuts, P.G.M., "Protective Groups in Organic Chemistry", $2^{nd}$, John Wiley & Sons, (1999) (Table of Contents Only).

Halford, et al., "Serotonergic Drugs: Effects on Appetite Expression and Use for the Treatment of Obesity" *Drugs* (2007) 67(1): 27-55.

Holenz, et al., "Medicinal chemistry strategies to 5-$HT_6$ receptor ligands as potential cognitive enhancers and antiobesity agents" *Drugs Discovery Today* (2006) 11: 283-299.

Johnson, et al., "5-$HT_6$ receptor antagonists: Prospects for the treatment of cognitive disorders including dementia" *Current Opinion in Drug Discovery & Development* (2008) 11(5): 642-654.

King, et al., "5-$HT_6$ receptor antagonists reverse delay-dependent deficits in novel object discrimination by enhancing consolidation—an effect sensitive to NMDA receptor antagonism" *Neuropharmacology* (2004) 47: 195-204.

King, et al., "A role for the 5-$HT_{1A}$, 5-$HT_4$ and 5-$HT_6$ receptors in learning and memory" *Trends in Pharmacological Sciences* (2008) XXX(X): 1-11.

Loiseau, et al., "Pro-cognitive effects of 5-$HT_6$ receptor antagonists in the social recognition procedure in rats: implication of the frontal cortex" *Psychopharmacology* (2008) 196: 93-104.

Marcos, et al., "Effects of 5-$HT_6$ receptor antagonism and cholinesterase inhibition in models of cognitive impairment in the rat" *Brit. J. Pharm.* (2008) 155: 434-440.

Mitchell, Ellen S. and John F. Neumaier, "5-$HT_6$ receptor antagonist reversal of emotional learning and prepulse inhibition deficits induced by apomorphine or scopolamine" *Pharmacology, Biochemistry and Behavior* (2008) 88: 291-298.

Pitsikas, et al., "The selective 5-$HT_6$ receptor antagonist Ro 04-6790 attenuates psychotomimetic effects of the NMDA receptor antagonist MK-801" *Manuscript* (2007) pp. 1-25.

Schreiber, et al., "Effects of the novel 5-$HT_6$ receptor antagonist RO4368554 in rat models for cognition and sensorimotor gating" *European Neuropsychopharmacology* (2007) 17: 277-288.

Wolley, et al., "Reversal of a cholinergic-induced deficit in a rodent model of recognition memory by the selective 5-$HT_6$ receptor antagonists, RO 04-6790" *Psychopharmacology* (2003) 170: 358-367.

*Controlled Drug Delivery*, vol. 1, Basic Concepts, Bruck, S.D. (Ed.) CRC Press, Inc., Boca Raton, Florida (1983) (Table of Contents Only).

*Encyclopdia of Pharmaceutical Technology*, $2^{nd}$ Ed., Swarbrick, J. and Boylan, J.C. (Eds.), Marcel Dekker, Inc., New York (2002) (Table of Contents Only).

*Handbook of Pharmaceutical Controlled Release Technology*, Wise, D.L. (Ed.), Marcel Dekker, Inc., New York (2000) (Table of Contents Only).

*The Theory and Practice of Industrial Pharmacy*, Lachman, L., Lieberman, H., and Kanig, J. (Eds.), Lea & Febiger, Philadelphia (1986) (Table of Contents Only).

*Modern Pharmaceutics*, $4^{th}$ Ed. Banker, G.S., and Rhodes, C.T. (Eds.), Marcel Dekker, Inc, New York (2002) (Table of Contents Only).

*Modified-Release Drug Technology*, Rathbone, M.J., Hadgraft, J., and Roberts, M.S. (Eds.), Marcel Dekker, Inc., New York (2002) (Table of Contents Only).

*Pharmaceutics: The Science of Dosage Forms*, $2^{nd}$ Ed. Aultonm, M.E. (Ed.) Churchill Livingstone, Edinburgh (2002) (Table of Contents Only).

* cited by examiner

SUBSTITUTED TETRAHYDRO-QUINOLINE-SULFONAMIDE COMPOUNDS, THEIR PREPARATION AND USE AS MEDICAMENTS

CROSS-REFERENCE TO RELATED APPLICATIONS

The present application claims the benefit under 35 U.S.C. 119(a)-(d) of European Patent Application No. 07380216.7, filed on Jul. 19, 2007, the entire contents of which are incorporated herein by reference.

FIELD OF THE INVENTION

The present invention relates to substituted tetrahydro-quinoline-sulfonamide compounds of general formula (I)

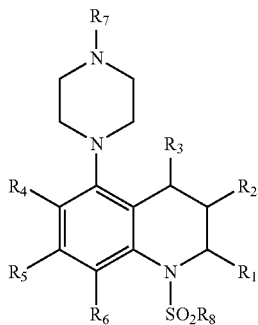

(I)

a method for their preparation, a medicament comprising these compounds and the use of substituted tetrahydro-quinoline-sulfonamide compounds for the preparation of medicaments for $5\text{-HT}_6$ receptor regulation as well as for the treatment and/or prophylaxis of disorders related thereto.

The new compounds of formula (I) show affinity for $5\text{-HT}_6$ receptors and are, therefore, effective for treating diseases mediated by these receptors.

BACKGROUND OF THE INVENTION

The superfamily of serotonin receptors (5-HT) includes 7 classes ($5\text{-HT}_1\text{-}5\text{-HT}_7$) encompassing 14 human subclasses [D. Hoyer, et al., *Neuropharmacology*, 1997, 36, 419]. The $5\text{-HT}_6$ receptor is the latest serotonin receptor identified by molecular cloning both in rats [F. J. Monsma, et al., *Mol. Pharmacol.*, 1993, 43, 320; M. Ruat, et al., *Biochem. Biophys. Res. Commun.*, 1993, 193, 268] and in humans [R. Kohen, et al., *J. Neurochem.*, 1996, 66, 47].

Compounds with $5\text{-HT}_6$ receptor affinity are useful for the treatment of various disorders of the Central Nervous System and of the gastrointestinal tract, such as irritable intestine syndrome. Compounds with $5\text{-HT}_6$ receptor affinity are also useful in the treatment of anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606].

Moreover, it has been shown that the $5\text{-HT}_6$ receptor also plays a role in food ingestion [*Neuropharmacology*, 2001, 41, 210-219]. Food ingestion disorders, particularly obesity, are a serious, fast growing threat to the health of humans of all age groups, since they increase the risk of developing other serious, even life-threatening diseases such as diabetes or coronary diseases.

Several patent documents refer to compounds with affinity for receptors of the 5-HT superfamily. Documents WO 96/23783, WO 96/02537, WO 96/11929 and WO 97/08167 describe heterocyclic compounds antagonists of 5-HT2b/2c.

Surprisingly, the authors of the present invention have observed that tetrahydro-quinoline-sulfonamide compounds with general formula (I) show an affinity for $5\text{-HT}_6$ receptors ranging from good to excellent. These compounds are therefore particularly suitable as pharmacologically active agents in medicaments for the prophylaxis and/or treatment of disorders or diseases related to $5\text{-HT}_6$ receptors.

OBJECT OF THE INVENTION

First of all, an object of the present invention is a tetrahydro-quinoline-sulfonamide derivative of general formula (I):

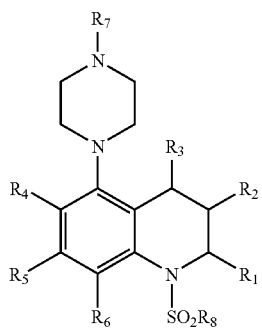

(I)

Compounds with general formula (I) have shown a high affinity for $5\text{HT}_6$ receptors and thus provide a good therapeutic alternative for treating disorders mediated by said receptors.

Another object of the present invention is a method for producing the tetrahydro-quinoline-sulfonamide compounds of general formula (I).

An additional object of the present invention is an intermediate of general formula (II):

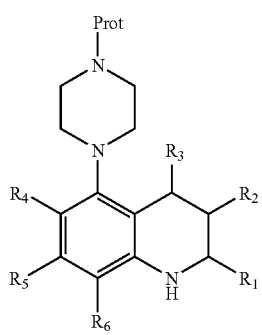

(II)

for obtaining the compounds of formula (I).

Another object of the present invention is to provide the novel tetrahydro-quinoline-sulfonamide compounds that are suitable in particular as active substances in medicaments, preferably in medicaments for the regulation of 5-HT$_6$ receptors, for cognitive enhancement, for the prophylaxis and/or treatment of food-intake related disorders, disorders of the central nervous system, disorders of the gastrointestinal tract, such as irritable intestine syndrome, anxiety, panic, depression, cognitive memory disorders, senile dementia disorders, such as Morbus Alzheimer, Morbus Parkinson and Morbus Huntington, schizophrenia, psychosis, infantile hyperkinesia, ADHD (attention deficit, hyperactivity disorders) and other 5-HT$_6$ mediated disorders particularly in mammals, including humans.

Likewise, an additional object of the present invention is the use of tetrahydro-quinoline -sulfonamide compounds of general formula (I) in the manufacture of a medicament for cognitive enhancement, for the prophylaxis and/or treatment of food ingestion (food intake) disorders, particularly for the regulation of appetite, for the maintenance, increase or reduction of body weight, for the prophylaxis and/or treatment of obesity, bulimia, anorexia, cachexia or type II diabetes (Non-insulin Dependent Diabetes Mellitus), preferably type II diabetes, which is caused by obesity, disorders of the central nervous system, disorders of the gastrointestinal tract, such as irritable intestine syndrome, anxiety, panic, depression, cognitive memory disorders, senile dementia disorders, such as Morbus Alzheimer, Morbus Parkinson and Morbus Huntington, schizophrenia, psychosis, infantile hyperkinesia, ADHD (attention deficit, hyperactivity disorders) and other 5-HT$_6$ mediated disorders particularly in mammals, including man.

DETAILED DESCRIPTION OF THE INVENTION

A first aspect of the invention refers to tetrahydro-quinoline-sulfonamide compounds of general formula (I)

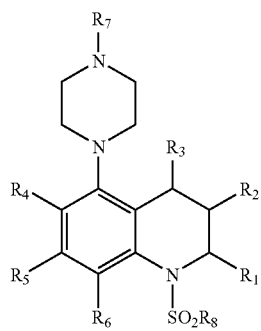

(I)

wherein $R_1$, $R_2$ and $R_3$, independent from one another, each represent a hydrogen atom; or a linear or branched, saturated or unsaturated $C_{1-6}$ aliphatic radical which may be substituted with 1, 2 or 3 substituent(s) independently selected from the group consisting of F, Cl, Br, —OH, —O—CH$_3$, —O—C$_2$H$_5$, —CN and —NRaRb, wherein Ra and Rb, independent from one another, each represents a hydrogen atom; or a linear or branched, saturated or unsaturated, unsubstituted or at least mono-substituted $C_{1-6}$ aliphatic radical; or Ra and Rb together with the bridging nitrogen atom form a saturated or unsaturated, unsubstituted or at least mono-substituted, optionally at least one additional heteroatom as ring member containing $C_{3-9}$ heterocycloaliphatic radical, which may be condensed with an unsubstituted or at least mono-substituted saturated, unsaturated or aromatic mono- or bicyclic ring system; or Ra and Rb together with the bridging nitrogen atom form an unsubstituted or at least mono-substituted, optionally at least one additional heteroatom as ring member containing $C_{5-14}$ heteroaryl radical, which may be condensed with an unsubstituted or at least mono-substituted saturated, unsaturated or aromatic mono- or bicyclic ring system;

with the proviso that at least one of $R_1$, $R_2$ and $R_3$ is a $C_{1-6}$ alkyl group optionally substituted with 1, 2 or 3 substituent(s) as defined above;

$R_4$, $R_5$ and $R_6$, independent from one another, each represent a hydrogen atom or a halogen atom;

$R_7$ represents a hydrogen atom; or a linear or branched, saturated or unsaturated $C_{1-6}$ aliphatic radical which may be substituted with 1, 2 or 3 substituent(s) independently selected from the group consisting of F, —OH, —O—CH$_3$ and —O—C$_2$H$_5$; and $R_8$ represents a 5- to 14-membered aryl or heteroaryl radical, which may be substituted with 1, 2 or 3 substituent(s) independently selected from the group consisting of $C_{1-5}$-alkyl, —O—C$_{1-5}$-alkyl, —S—C$_{1-5}$-alkyl, —C(═O)—OH, —C(═O)—O—C$_{1-5}$-alkyl, —O—C(═O)—C$_{1-5}$-alkyl, F, Cl, Br, I, —CN, —CF$_3$, —OCF$_3$, —SCF$_3$, —OH, —SH, —NH$_2$, —NH(C$_{1-5}$-alkyl), —N(C$_{1-5}$-alkyl)$_2$, —NH—C(═O)—C$_{1-5}$-alkyl, —N(C$_{1-5}$-alkyl)—C(═O)—C$_{1-5}$-alkyl, —NO$_2$, —CHO, —CF$_2$H, —CFH$_2$, —C(═O)—NH$_2$, —C(═O)—NH(C$_{1-5}$-alkyl), —C(═O)—N(C$_{1-5}$-alkyl)$_2$, —S(═O)$_2$—C$_{1-5}$-alkyl, —S(═O)$_2$-phenyl, cyclopropyl, cyclobutyl, cyclopentyl, cyclohexyl, phenyl, phenoxy, benzyloxy and benzyl, and which may be bonded via a linear or branched $C_{1-6}$ alkylene, $C_{2-6}$ alkenylene or $C_{2-6}$ alkinylene group, wherein the heteroaryl radical contains 1, 2 or 3 heteroatom(s) independently selected from N, O and S as members of the ring;

optionally in form of one of its stereoisomers, preferably enantiomers or diasteromers, a racemate or in form of a mixture of at least two of its stereoisomers, preferably enantiomers and/or diastereomers, in any mixing ratio, or a physiologically acceptable salt, isomer, prod rug or solvate thereof.

The term "condensed" according to the present invention means that a ring or ring system is attached to another ring or ring system, whereby the terms "annulated" or "annelated" are also used by those skilled in the art to designate this kind of attachment.

In a particular embodiment of the compounds of formula (I), $R_1$ $R_2$ and $R_3$, independent from one another, each represent a hydrogen atom; or a linear or branched $C_{1-6}$ alkyl radical which may be substituted with 1, 2 or 3 substituent(s) independently selected from the group consisting of F, Cl, Br, —OH, —O—CH$_3$, —O—C$_2$H$_5$, —CN and —NRaRb, wherein Ra and Rb, independent from one another, each represents a hydrogen atom; or a linear or branched, saturated or unsaturated, unsubstituted or at least mono-substituted $C_{1-3}$ alkyl radical; or Ra and Rb together with the bridging nitrogen atom form a saturated or unsaturated, unsubstituted or at least mono-substituted, optionally at least one additional heteroatom as ring member containing $C_{3-7}$ heterocycloalkyl radical, which may be condensed with an unsubstituted or at least mono-substituted saturated, unsaturated or aromatic mono- or bicyclic ring system; or Ra and Rb together with the bridging nitrogen atom form an unsubstituted or at least mono-substituted, optionally at least one additional heteroatom as ring member containing $C_{5-10}$ heteroaryl radical, which may be condensed with an unsubstituted or at least mono-substituted saturated, unsaturated or aromatic mono- or bicyclic ring system;

with the proviso that at least one of $R_1$, $R_2$ and $R_3$ is a $C_{1-6}$ alkyl group optionally substituted with 1, 2 or 3 substituent(s) as defined above.

In a preferred embodiment, $R_4$, $R_5$ and $R_6$, independent from one another, each represent a hydrogen atom or a chlorine atom; $R_7$ represents a hydrogen atom or a linear or branched $C_{1-6}$ alkyl radical which may be substituted with 1, 2 or 3 substituent(s) independently selected from the group consisting of F, —OH, —O—$CH_3$ and —O—$C_2H_5$; and $R_8$ represents a 6- to 10-membered aryl radical which may be substituted with 1, 2 or 3 substituent(s) independently selected from the group consisting of —$CH_3$, —$C_2H_5$, Cl, Br, —OH, —$NH_2$, —SH, —O—$CH_3$, —O—$C_2H_5$, —$NO_2$, —CN, —NH—$CH_3$ and —S—$CH_3$.

In another particular embodiment of the compounds of formula (I), $R_4$, $R_5$ and $R_6$, independent from one another, each represent a hydrogen atom or a chlorine atom; $R_7$ represents a hydrogen atom or a linear or branched $C_{1-6}$ alkyl radical which may be substituted with 1, 2 or 3 substituent(s) independently selected from the group consisting of F, —OH, —O—$CH_3$ and —O—$C_2H_5$, and $R_8$ represents a 6- to 10-membered aryl radical which may be substituted with 1, 2 or 3 substituent(s) independently selected from the group consisting of-$CH_3$, —$C_2H_5$, Cl, Br, —OH, —$NH_2$, —SH, —O—$CH_3$, —O—$C_2H_5$, —$NO_2$, —CN, —NH—$CH_3$ and —S—$CH_3$.

In a preferred embodiment, $R_1$, $R_2$ and $R_3$, independent from one another, each represent each represent a hydrogen atom; or a linear or branched $C_{1-6}$ alkyl radical which may be substituted with 1, 2 or 3 substituent(s) independently selected from the group consisting of F, Cl, Br, —OH, —O—$CH_3$, —O—$C_2H_5$, —CN and —NRaRb, wherein Ra and Rb, independent from one another, each represents a hydrogen atom; or a linear or branched, saturated or unsaturated, unsubstituted or at least mono-substituted $C_{1-3}$ alkyl radical; or Ra and Rb together with the bridging nitrogen atom form a saturated or unsaturated, unsubstituted or at least mono-substituted, optionally at least one additional heteroatom as ring member containing $C_{3-7}$ heterocycloalkyl radical, which may be condensed with an unsubstituted or at least mono-substituted saturated, unsaturated or aromatic mono- or bicyclic ring system; or Ra and Rb together with the bridging nitrogen atom form an unsubstituted or at least mono-substituted, optionally at least one additional heteroatom as ring member containing $C_{5-10}$ heteroaryl radical, which may be condensed with an unsubstituted or at least mono-substituted saturated, unsaturated or aromatic mono- or bicyclic ring system;

with the proviso that at least one of $R_1$, $R_2$ and $R_3$ is a $C_{1-6}$ alkyl group optionally substituted with 1, 2 or 3 substituent(s) as defined above.

In another particular embodiment, the tetrahydro-quinoline-sulfonamide of general formula (I) is selected from the following group:

[1] 1,2,3,4-Tetrahydro-2-methyl-5-(4-methylpiperazin-1-yl)-1-(4-methylbenzenesulfonyl)quinoline trifluoroacetate;

[2] 1,2,3,4-Tetrahydro-2-methyl-5-(piperazin-1-yl)-1-(4-methylbenzenesulfonyl)-quinoline trifluoroacetate;

[3] 1,2,3,4-Tetrahydro-2-methyl-5-(piperazin-1-yl)-1-(α-naphthylsulfonyl)quinoline trifluoroacetate;

[4] 1,2,3,4-Tetrahydro-2-methyl-5-(piperazin-1-yl)-1-(β-naphthylsulfonyl)quinoline trifluoroacetate;

[5] 1,2,3,4-Tetrahydro-2-methyl-5-(piperazin-1-yl)-1-(benzenesulfonyl)quinoline trifluoroacetate; and

[6] 1,2,3,4-Tetrahydro-2-methyl-5-(piperazin-1-yl)-1-(3-nitrophenylsulfonyl)quinoline trifluoroacetate.

Another aspect of the present invention relates to a method for the preparation of at least one tetrahydro-quinoline-sulfonamide of general formula (I) that comprises reacting a compound of general formula (II)

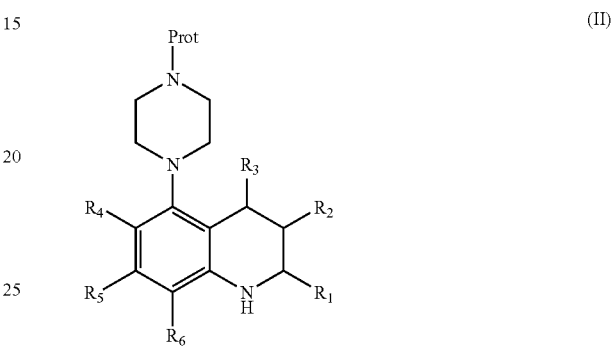

(II)

wherein $R_1$, $R_2$, $R_3$, $R_4$, $R_5$ and $R_6$ have the meanings previously given for general formula (I), and Prot is an N-protecting group;

with a sulfonyl derivative of general formula (III):

$R_8SO_2X$         (III)

wherein $R_8$ has the meaning previously given for general formula (I) and X is a leaving group, preferably halogen; for producing the compound of general formula (IV):

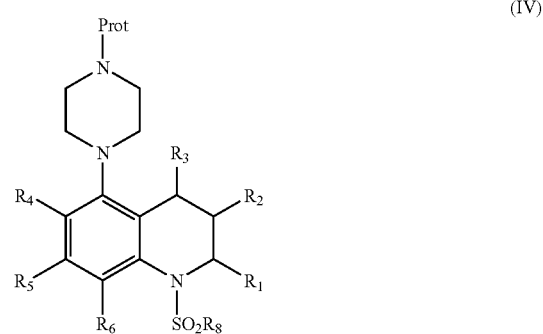

(IV)

wherein $R_1$, $R_2$, $R_3$, $R_4$, $R_5$, $R_6$ and $R_8$ have the meanings previously given for general formula (I), and Prot is an N-protecting group;

removing the N-protecting group for producing the compound of general formula (I) wherein $R_7$ represents a hydrogen atom; and optionally reacting the compound of general formula (I) wherein $R_7$ represents a hydrogen atom with a compound of general formula (V):

R'X         (V)

wherein X is a leaving group, preferably halogen, and R' represents a linear or branched, saturated or unsaturated $C_{1-6}$ aliphatic radical which may be substituted with 1, 2 or 3 substituent(s) independently selected from the group consisting of F, —OH, —O—CH$_3$ and —O—C$_2$H$_5$;

for producing the compound of general formula (I) wherein R$_7$ has the meaning previously given for general formula (I) except a hydrogen atom.

In the compounds of formula (II) Prot is any suitable conventional N-protecting group, preferably any of those described in the literature [Protective groups in Organic Chemistry, ed. J. F. W. McOmie, Plenum Press, 1973; T. W. Greene & P. G. M. Wuts, Protective Groups in Organic Chemistry, John Wiley & Sons, 1991] which may be removed in the suitable subsequent stage by methods known in the prior art. The respective literature descriptions are incorporated by reference and form part of the disclosure. More preferably, Prot is an N-protecting group selected from Fmoc (9-fluorophenylmethyloxycarbonyl), Alloc (allyloxycarbonyl) and Boc (tert-butoxycarbonyl); preferably Boc.

The reaction between the compounds of general formula (II) and (III) is usually carried out in the presence of an organic reaction medium, preferably in the presence of dialkyl ether, more preferably diethyl ether or a cyclic ether, more preferably tetrahydrofuran or dioxane, an halogenated organic hydrocarbon, more preferably methylene chloride or chloroform, an alcohol, more preferably methanol or ethanol, a dipolar aprotic solvent, more preferably acetonitrile, pyridine or dimethylformamide, or any other suitable reaction medium. Naturally, mixtures of at least two of the classes of the mentioned compounds or at least two compounds of one class may also be used.

The reaction is preferably carried out in the presence of a suitable base, for example, the presence of an inorganic base, more preferably alkaline metal hydroxides and alkaline metal carbonates, or in the presence of an organic base, more preferably triethylamine, N-ethyldiisopropylamine or pyridine.

The most suitable reaction temperatures range from 0° C. to room temperature, that is, approximately 25° C., and the reaction time is preferably from 5 minutes to 24 hours.

Compounds of general formula (III) are commercially available, or they may be prepared according to standard methods known in the prior art, for example by methods similar to those described in the literature [E. E. Gilbert, Synthesis, 1969, 1, 3].

Compounds of general formula (II) may be prepared by reduction of compounds of general formula (VII):

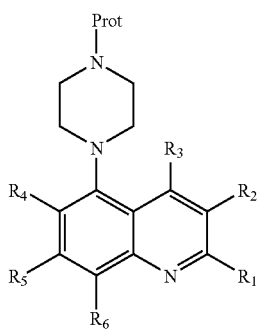

(VII)

Reduction preferably takes place with the aid of a metallic catalyst such as nickel chloride and a reducing agent such as sodium borohydride, according to the methodology disclosed in Nose et al. [Nose A., Kudo T., Chem. Pharm. Bull. 1984, 32, 2421]. The respective literature descriptions are incorporated by reference and form part of the disclosure.

When R$_2$, R$_3$, R$_4$, R$_5$ and R$_6$ are hydrogen, compounds of general formula (VII) can be prepared by reacting a compound of general formula (VIII):

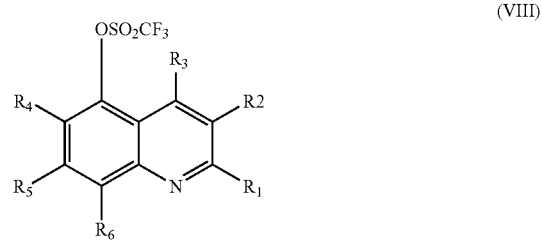

(VIII)

with a compound of general formula (IX)

(IX)

under reflux in the presence of an organic reaction medium such as toluene, a suitable base such as cesium carbonate, and a suitable catalytic system such as palladium acetate and 2,2'-bis(diphenylphosphino)-1,1'-binaphthyl.

Compounds of general formula (IX) are commercially available or can be prepared according to the methodology disclosed in the literature [Bradbury et al., J. Med. Chem. 1991, 34, 1078]. The respective literature descriptions are incorporated by reference and form part of the disclosure.

Compounds of general formula (VIII) can be prepared by reacting a compound of general formula (X):

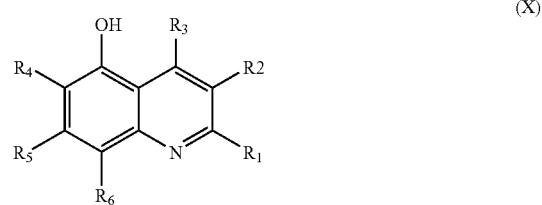

(X)

with trifluoromethanesulfonic anhydride: $(F_3CSO_2)_2O$ according to the methodology disclosed in the literature [WO 2005/014552]. The respective literature descriptions are incorporated by reference and form part of the disclosure.

Compounds of general formula (X) can be prepared by reacting a compound of general formula (XI):

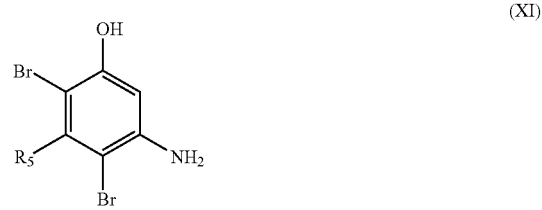

(XI)

with the corresponding alkylene aldehyde of formula (XII):

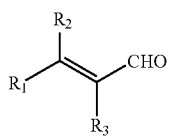

(XII)

according to the methodology disclosed in the literature [Choi et al., *J. Am. Chem. Soc.* 2001, 123, 9203]. The respective literature descriptions are incorporated by reference and form part of the disclosure.

Compounds of general formula (XI) can be prepared by hydrolyzing a compound of general formula (XIII):

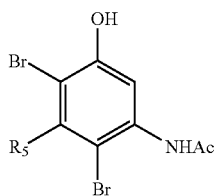

(XIII)

with a suitable acid.

Compounds of general formula (XIII) can be prepared by reacting a compound of general formula (XIV)

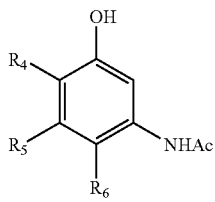

(XIV)

with a suitable brominating reagent such as benzyltrimethylammonium chlorobromate according to the methodology disclosed in the literature [Kajigaeshi et al., *J. Am. Chem. Soc. Jpn.* 1998, 61, 2681]. The respective literature descriptions are incorporated by reference and form part of the disclosure.

Compounds of general formula (XIV) can be prepared by reacting a compound of general formula (XV)

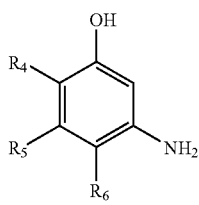

(XV)

with acetic anhydride according to the methodology disclosed in the literature [Sarvari et al., *Tetrahedron* 2005, 61, 10903]. The respective literature descriptions are incorporated by reference and form part of the disclosure.

Once the compounds of general formula (II) are prepared and reacted with the compounds of general formula (III) for obtaining the sulfonamide compounds of general formula (IV), these latter are then deprotected in order to obtain the compounds of general formula (I) wherein $R_7$ represents a hydrogen atom. The removal of the N-protecting group is carried out by methods known in the prior art as previously indicated by using a suitable acid such as trifluoroacetic acid (TFA).

Optionally, the compounds of general formula (I) wherein $R_7$ represents a hydrogen atom are subsequently reacted with a compound of general formula (V):

R'X   (V)

wherein X is a leaving group, preferably halogen, and R' represents a linear or branched, saturated or unsaturated $C_{1-6}$ aliphatic radical which may be substituted with 1, 2 or 3 substituent(s) independently selected from the group consisting of F, —OH, —O—$CH_3$ and —O—$C_2H_5$; in order to obtain the compounds of general formula (I) wherein $R_7$ has the meaning previously given for general formula (I) except a hydrogen atom.

The reaction between the compounds of general formula (I) wherein $R_7$ is hydrogen and the compounds of general formula (V) is usually carried out in the presence of in the presence of an organic reaction medium, more preferably dialkyl ether, even more preferably diethyl ether, or a cyclic ether, even more preferably tetrahydrofuran or dioxane, an hydrocarbon, even more preferably toluene, an alcohol, even more preferably methanol or ethanol, a dipolar aprotic solvent, even more preferably acetonitrile, pyridine or dimethylformamide, or any other suitable reaction medium. Naturally, mixtures of at least two of the classes of the mentioned compounds or at least two compounds of one class may also be used.

This reaction is carried out preferably in the presence of a suitable base, more preferably in the presence of alkaline metal hydroxides and alkaline metal carbonates, metal hydrides, metal alkoxides, even more preferably sodium hydride, sodium methoxide or potassium tert-butoxide, organometallic compounds, even more preferably butyllithium or tert-butyllithium.

The most suitable reaction temperatures range from 0° C. to the boiling temperature of the reaction medium, and the reaction times are preferably from 1 to 24 hours.

The general process for the preparation of compounds of general formula (I) as described above is also depicted in general Scheme I:

Scheme I

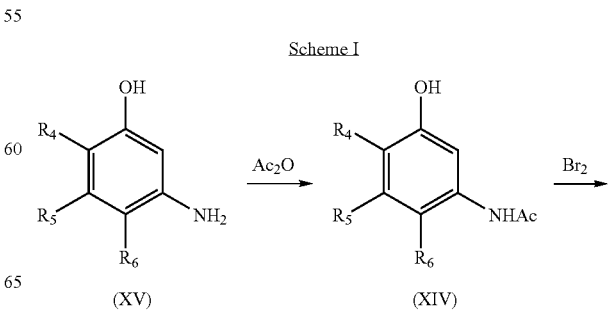

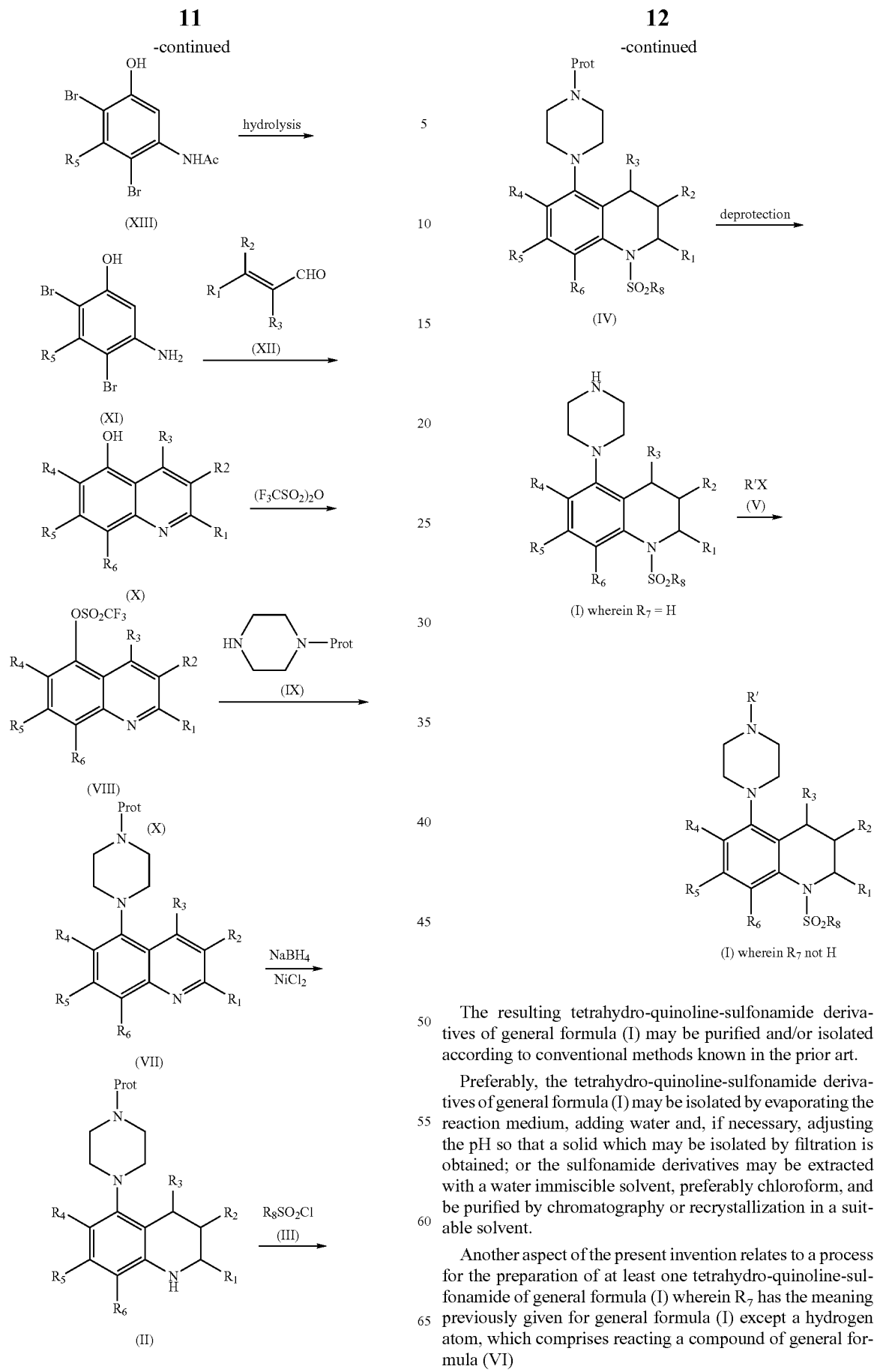

The resulting tetrahydro-quinoline-sulfonamide derivatives of general formula (I) may be purified and/or isolated according to conventional methods known in the prior art.

Preferably, the tetrahydro-quinoline-sulfonamide derivatives of general formula (I) may be isolated by evaporating the reaction medium, adding water and, if necessary, adjusting the pH so that a solid which may be isolated by filtration is obtained; or the sulfonamide derivatives may be extracted with a water immiscible solvent, preferably chloroform, and be purified by chromatography or recrystallization in a suitable solvent.

Another aspect of the present invention relates to a process for the preparation of at least one tetrahydro-quinoline-sulfonamide of general formula (I) wherein $R_7$ has the meaning previously given for general formula (I) except a hydrogen atom, which comprises reacting a compound of general formula (VI)

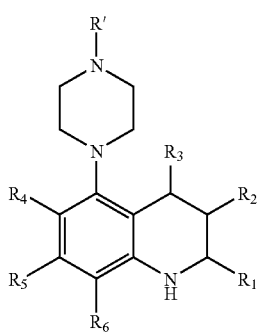

(VI)

wherein $R_1$, $R_2$, $R_3$, $R_4$, $R_5$ and $R_6$ have the meanings previously given for general formula (I), and R' is a linear or branched, saturated or unsaturated $C_{1-6}$ aliphatic radical which may be substituted with 1, 2 or 3 substituent(s) independently selected from the group consisting of F, —OH, —O—$CH_3$ and —O—$C_2H_5$;
with a sulfonyl derivative of general formula (III):

$$R_8SO_2X \quad (III)$$

wherein $R_8$ has the meaning previously given for general formula (I) and X is a leaving group, preferably halogen.

The reaction between the compounds of general formula (VI) and (III) is usually carried out in the presence of in the presence of an organic reaction medium, more preferably dialkyl ether, even more preferably diethyl ether, or a cyclic ether, even more preferably tetrahydrofuran or dioxane, an hydrocarbon, even more preferably toluene, an alcohol, even more preferably methanol or ethanol, a dipolar aprotic solvent, even more preferably acetonitrile, pyridine or dimethylformamide, or any other suitable reaction medium. Naturally, mixtures of at least two of the classes of the mentioned compounds or at least two compounds of one class may also be used.

This reaction is carried out preferably in the presence of a suitable base, more preferably in the presence of alkaline metal hydroxides and alkaline metal carbonates, metal hydrides, metal alkoxides, even more preferably sodium hydride, sodium methoxide or potassium tert-butoxide, organometallic compounds, even more preferably butyllithium or tert-butyllithium.

The most suitable reaction temperatures range from 0° C. to the boiling temperature of the reaction medium, and the reaction times are preferably from 1 to 24 hours.

The compounds of general formula (VI) are obtained by reduction of compounds of general formula (VII)'

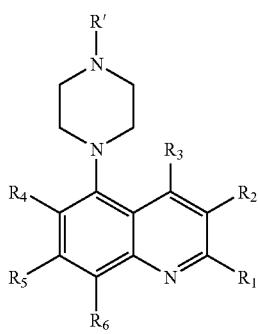

(VII)' according to a process analogous as that described above for the preparation of compounds of general formula (II).

In general Scheme II the general process is depicted for preparing the compounds of general formula (I) wherein $R_7$ has the meaning previously given for general formula (I) except a hydrogen atom:

Scheme II:

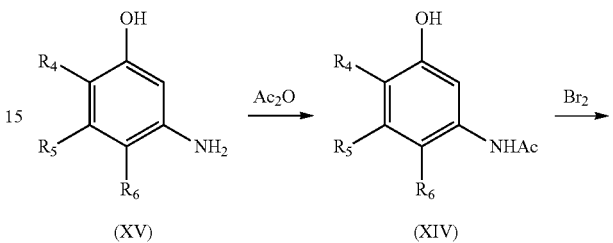

(XV)          (XIV)

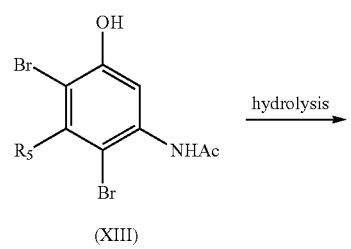

(XIII)

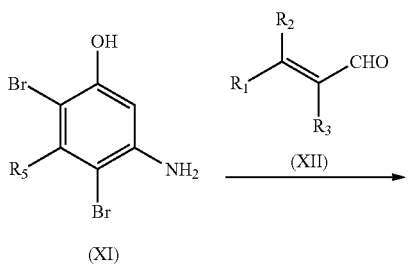

(XI)          (XII)

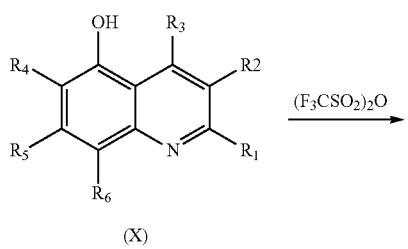

(X)

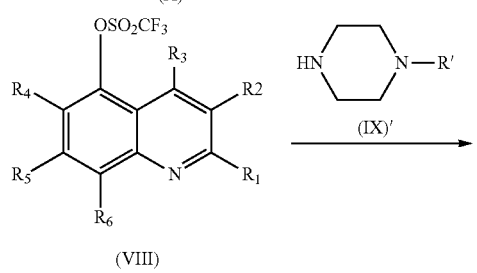

(VIII)

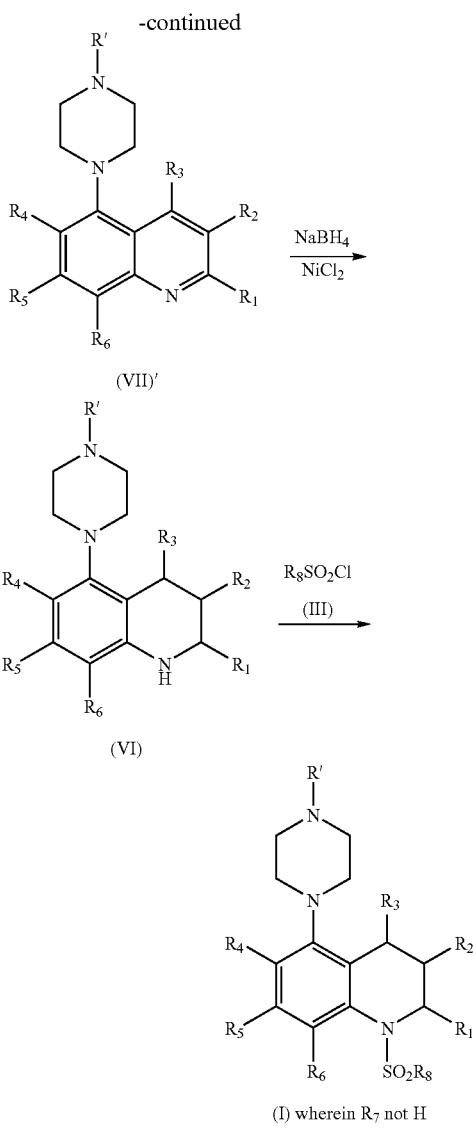

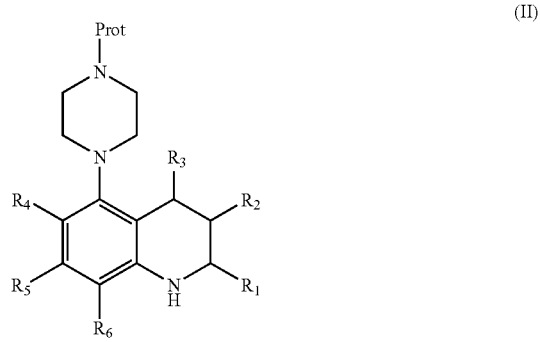

(I) wherein R7 not H

Preferably, the resulting tetrahydro-quinoline-sulfonamide derivatives of general formula (I) may be isolated by filtration, concentrating the filtrate under reduced pressure, adding water and, if necessary, adjusting the pH so that a solid which may be isolated by filtration is obtained; or the sulfonamide derivatives may be extracted with a water immiscible solvent, preferably chloroform, and be purified by chromatography or recrystallization in a suitable solvent, as previously disclosed.

If the tetrahydro-quinoline-sulfonamide derivatives of general formula (I) are obtained in form of a mixture of stereoisomers, preferably enantiomers or diastereomers, said mixtures may be separated via standard processes known in the prior art, for example chromatographic methods or crystallization with chiral agents.

The compounds of general formula (I) and stereoisomers thereof may be obtained in form of a corresponding salt according to methods well known to those skilled in the art, e.g. by reacting said compound with at least one inorganic and/or organic acid, preferably in a suitable reaction medium. Suitable reaction media include, for example, any of the ones given above. Suitable inorganic acids include but are not limited to hydrochloric acid, hydrobromic acid, phosphoric acid, oxalic acid, sulfuric acid, nitric acid, suitable organic acids include but are not limited to citric acid, maleic acid, fumaric acid, trifluoroacetic acid, tartaric acid, or derivatives thereof, p-toluenesulfonic acid, methanesulfonic acid or camphersulfonic acid.

The term "salt" is to be understood as meaning any form of the substituted tetrahydro-quinoline-sulfonamide compounds in which they assume an ionic form or are charged and are coupled with a counter-ion (a cation or anion) or are in solution. By this are also to be understood complexes of the active compound with other molecules and ions, in particular complexes which are complexed via ionic interactions.

The term "physiologically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, trifluoroacetic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

Solvates, preferably hydrates, of the substituted tetrahydro-quinoline-sulfonamide compounds of general formula (I) and of corresponding stereoisomers may also be obtained by standard procedures known to those skilled in the art.

The term "solvate" according to this invention is to be understood as meaning any form of the substituted tetrahydro-quinoline-sulfonamide compounds in which they have attached to it via non-covalent binding another molecule (most likely a polar solvent) especially including hydrates and alcoholates, e.g. methanolate.

Another aspect of the invention is an intermediate compound of general formula (II):

wherein $R_1$, $R_2$, $R_3$, $R_4$, $R_5$ and $R_6$ have the meanings previously given for general formula (I), and Prot is an N-protecting group.

In a particular embodiment of the compounds of general formula (II), Prot is an N-protecting group selected from Fmoc, Alloc and Boc; preferably Boc.

In another particular embodiment, the compound of general formula (II) is selected from the following group:

[i] tert-Butyl 4-(1,2,3,4-tetrahydro-2-methylquinolin-5-yl)piperazine-1-carboxylate;
[ii] tert-Butyl 4-(1,2,3,4-tetrahydro-3-methylquinolin-5-yl)piperazine-1-carboxylate; and
[iii] tert-Butyl 4-(1,2,3,4-tetrahydro-3-ethylquinolin-5-yl)piperazine-1-carboxylate A further aspect of the present invention relates to a medicament comprising at least one of substituted tetrahydro-quinoline-sulfonamide compounds of general formula (I) optionally in form of one of its stereoisomers, preferably enantiomers or diasteromers, a racemate or in form of a mixture of at least two stereoisomers, preferably enantiomers and/or diastereomers, in any mixing ratio, or a physiologically acceptable salt thereof, or a corresponding solvate thereof, and optionally at least one physiologically acceptable auxiliary agent.

As already mentioned, the tetrahydro-quinoline-sulfonamide compounds of general formula (I) have a strong affinity to $5\text{-HT}_6$ receptors and can behave as agonists, antagonists, inverse agonists, partial antagonists or partial agonists thereof. For this reason, the medicaments comprising at least one of them are particularly suitable for $5\text{-HT}_6$ receptor regulation and therefore for the prophylaxis and/or treatment of a disorder or a disease that is least partially mediated via $5\text{-HT}_6$ receptors.

In a preferred embodiment of the present invention said medicament is suitable for the prophylaxis and/or treatment of food intake disorders, preferably for the regulation of appetite, for the maintenance, increase or reduction of body weight, for the prophylaxis and/or treatment of obesity, for the prophylaxis and/or treatment of bulimia, for the prophylaxis and/or treatment of anorexia, for the prophylaxis and/or treatment of cachexia, for the prophylaxis and/or treatment of type II diabetes (non-insulin dependent diabetes mellitus); for the prophylaxis and/or treatment of cognitive disorders, preferably memory disorders; or for improvement of cognition (for cognitive enhancement).

In another preferred embodiment of the present invention, said medicament is suitable for the prophylaxis and/or treatment of gastrointestinal disorders, preferably irritable colon syndrome; for the prophylaxis and/or treatment of disorders of the central nervous system; for the prophylaxis and/or treatment of anxiety; for the prophylaxis and/or treatment panic attacks; for the prophylaxis and/or treatment of depression; for the prophylaxis and/or treatment of bipolar disorders; for the prophylaxis and/or treatment of senile dementia; for the prophylaxis and/or treatment of psychosis; for the prophylaxis and/or treatment neurodegenerative disorders; preferably selected from the group consisting of Morbus Alzheimer, Morbus Parkinson, Morbus Huntington and Multiple Sclerosis; for the prophylaxis and/or treatment of schizophrenia or for the prophylaxis and/or treatment hyperactivity disorder (ADHD, attention deficit, hyperactivity disorder).

The medicament obtained according to the present invention is particularly suitable for the administration to mammals, including man. The drug can preferably be administered to all age groups, namely, children, adolescents and adults.

Another aspect of the present invention is the use of at least one substituted tetrahydro-quinoline-sulfonamide of general formula (I), optionally in form of one of its stereoisomers, preferably enantiomers or diasteromers, a racemate or in form of a mixture of at least two stereoisomers, preferably enantiomers and/or diastereomers, in any mixing ratio, or a physiologically acceptable salt thereof, or a corresponding solvate, for the manufacture of a medicament for $5\text{-HT}_6$ receptor regulation or for the prophylaxis and/or treatment of disorders that are at least partially mediated via 5-HT6 receptors.

In a particular embodiment of the present invention, the tetrahydro-quinoline-sulfonamides of general formula (I) are used in the manufacture of a medicament for the prophylaxis and/or treatment of food intake disorders; for the prophylaxis and/or treatment of cognitive disorders; or for improvement of cognition (for cognitive enhancement). In a preferred embodiment, the tetrahydro-quinoline-sulfonamides of general formula (I) are used in the manufacture of a medicament for the regulation of appetite, for the reduction, increase or maintenance of body weight; for the prophylaxis and/or treatment of obesity, for the prophylaxis and/or treatment of bulimia, for the prophylaxis and/or treatment of anorexia; for the prophylaxis and/or treatment of cachexia; for the prophylaxis and/or treatment of type II diabetes; or for the prophylaxis and/or treatment of memory disorders.

In another particular embodiment of the present invention, the tetrahydro-quinoline -sulfonamides of general formula (I) are used in the manufacture of a medicament for the prophylaxis and/or treatment of gastrointestinal disorders, preferably irritable colon syndrome; for the prophylaxis and/or treatment of disorders of the central nervous system; for the prophylaxis and/or treatment of anxiety; for the prophylaxis and/or treatment panic attacks; for the prophylaxis and/or treatment of depression; for the prophylaxis and/or treatment of bipolar disorders; for the prophylaxis and/or treatment of senile dementia; for the prophylaxis and/or treatment of psychosis; for the prophylaxis and/or treatment neurodegenerative disorders; preferably selected from the group consisting of Morbus Alzheimer, Morbus Parkinson, Morbus Huntington and Multiple Sclerosis; for the prophylaxis and/or treatment of schizophrenia; or for the prophylaxis and/or treatment hyperactivity disorder (ADHD, attention deficit, hyperactivity disorder).

Any medicament according to the present invention may be in any form suitable for the application to humans and/or animals, preferably humans including infants, children and adults. The medicament can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S, and Rhodes C. T. (Eds.) Marcel Dekker, Inc. New York 2002 and "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The composition of the medicament may vary depending on the route of administration.

The medicament of the present invention may, for example, be administered parenterally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, granules, capsules, lozenges, aqueous or oily solutions, suspensions, emulsions, or dry powdered forms suitable for reconstitution with water or other suitable liquid medium before use, for immediate or retarded release. The multiparticulate forms, such as pellets or granules, may e.g. be filled into a capsule, compressed into tablets or suspended in a suitable liquid.

Suitable controlled release formulations, materials and methods for their preparation are known from the prior art, e.g. from the table of contents of "Modified-Release Drug Delivery Technology", Rathbone, M. J. Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York, (2000); "Controlled Drug Delivery", Vol, I, Basic Concepts, Bruck, S. D. (Ed.), CRD Press Inc., Boca Raton (1983) y de Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective descriptions are hereby incorporated by reference and form part of the disclosure.

Medicaments according to the present invention may also comprise an enteric coating, so that their dissolution is dependent on pH-value. Due to said coating the medicament can pass the stomach undissolved and the respective tetrahydro-quinoline-sulfonamide compound is liberated in the intestinal tract. Preferably the enteric coating is soluble at a pH value of 5 to 7.5. Suitable materials and methods for the preparation are known from the prior art.

Typically, the medicaments according to the present invention may contain 1-60% by weight of one or more substituted tetrahydro-quinoline-sulfonamide compounds as defined herein and 40-99% by weight of one or more auxiliary substances (additives).

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 0.01 to 4000 mg, preferably 0.1 to 2000 mg, more preferably 0.5 to 1000 of active substance to be administered during one or several intakes per day.

The present invention is illustrated below with the aid of examples. These illustrations are given solely by way of example and do not limit the general spirit of the present invention.

EXAMPLES

Example 1

Preparation of 3-acetylaminophenol

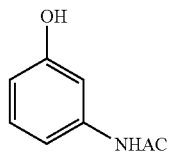

To a stirred mixture of 3-aminophenol (10 g, 91 mmol) and ZnO (8 g) was added acetic anhydride (10 mL, 92 mmol). The reaction mixture was stirred at room temperature for 15 min, dissolved in acetone (50 mL), the precipitate was filtered off, the filtrate was washed with acetone, and the solvent was evaporated in vacuo. The diacyl compound was dissolved in MeOH (130 mL) and after adding saturated solution of NaHCO$_3$ the mixture was heated under reflux for 1 h. The solvent was evaporated in vacuo, the residue was acidified with HCl, and then extracted with EtOAc. The organic solution was dried and evaporation of solvent afforded crude monoacetylated compound (12.7 g) which was recrystallized from a mixture of CH$_2$Cl$_2$-MeOH (20:1). The precipitate was filtered and washed with CH$_2$Cl$_2$-MeOH until a white solid.

Yield: 11.5 g (83.6%); R$_f$=0.6 (CH$_2$Cl$_2$-MeOH 9:1).

Example 2

Preparation of N-(2,4-dibromo-5-hydroxyphenyl)acetamide

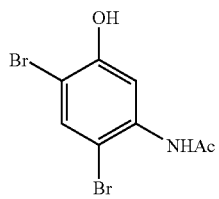

10 g (66 mmol) of the compound prepared in example 1 was dissolved in 200 mL MeOH and 700 mL CH$_2$Cl$_2$ was added. Benzyltrimethylammonium chlorobromate (2 eq, 45.7 g) was added during 1 hour, then the mixture was stirred for 15 min at room temperature (More reagent was added when necessary). The solvent was evaporated and to the residue water was added (500 mL). The mixture was extracted 4× with ether (1 L). After evaporating the solvent, the crude product was washed with CH₂Cl₂ to obtain brown-white crystals. Yield: 15 g (73.5%); $R_f$=0.47 (CH₂Cl₂-MeOH 19:1).

Example 3

Preparation of 5-amino-2,4-dibromophenol

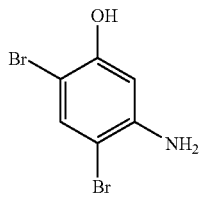

A suspension of 15 g of the compound prepared in example 2 in 70 mL 30% HCl and 200 mL water was refluxed for 3 h. The suspension was neutralized with NaOAc. The precipitate was collected, the mother liquor was extracted with EtOAc, dried (MgSO₄), evaporated. The collected products was washed 3× with water.

Yield: 12.9 g (99%); $R_f$=0.28 (hexane-acetone 5:2).

Example 4

Preparation of 2-methylquinolin-5-ol

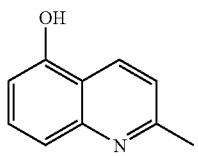

To a stirred mixture of the 5-amino-2,4-dibromophenol prepared in example 3 (13 g, 49 mmol), acetic acid (65 mL) and HCl (65 mL) was added crotonaldehyde and the resultant mixture was heated at reflux for 1.5 h under argon. HBr (65 mL) and aniline (13 mL) were added and the mixture was refluxed for 5 h. After cooling, the reaction mixture was neutralized by adding of NaHCO₃ (~180 g) and then extracted with EtOAc. The organic extract was dried (MgSO₄) and concentrated in vacuo to give a black solid (22 g). The crude product was purified by column chromatography (eluents: CH₂Cl₂-MeOH 98:2). Yield 5 g (49%) brown-white solid. $R_f$=0.43 (CH₂Cl₂-MeOH 9:1).

Example 5

Preparation of 2-methylquinolin-5-yl trifluoromethanesulfonate

To a stirred and cooled solution of the 2-methylquinolin-5-ol prepared in example 4 (2.3 g, 14.4 mmol) and pyridine (5.9 mL) in CH₂Cl₂ (40 mL) was added dropwise trifluoromethanesulfonic anhydride (3.8 mL, 22.6 mmol) and the resulting mixture was stirred at room temperature for 1 h, under Ar. The reaction mixture was poured onto water (15 mL) and extracted with EtOAc. The organic extract was dried over MgSO₄ and concentrated in vacuo. The crude product was purified by column chromatography using hexane-acetone 10:1 as eluent. Yield: 3.95 g (93.8%), yellow oil. $R_f$=0.42 (hexane-acetone 10:4).

Example 6

Preparation of tert-butyl 4-(2-methylquinolin-5-yl)piperazine-1-carboxylate.

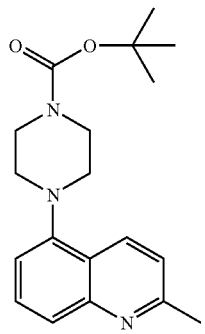

A stirred mixture of Pd(OAc)₂ (243 mg), CsCO₃ (6.63 g), and 2,2'-bis(diphenylphosphino)-1,1'-binaphthyl (1.01 g) in dry toluene (60 mL) was heated under reflux for 15 min, under argon. After cooling, a solution of tert-butyl piperazine-1-carboxylate (3.03 g, 16.3 mmol) and the 2-methylquinolin-5-yl trifluoromethane-sulfonate prepared in example 5 (3.95 g, 13.6 mmol) in toluene (100 mL) was added, and the resulting mixture was heated under reflux for 8 h. The reaction mixture was cooled to room temperature, concentrated to half of its value, and then quenched with saturated solution of NH₄Cl (50 mL). The organic layer was separated, the aqueous layer was extracted with EtOAc, and the combined organic solutions were concentrated in vacuo. The residue was purified by column chromatography using CH₂Cl₂ as eluent. Yield: 4.29 g (96.6%), brown oil. $R_f$=0.64 (CH₂Cl₂-MeOH (19:1).

Example 7

Preparation of tert-butyl 4-(1,2,3,4-tetrahydro-2-methylquinolin-5-yl)piperazine-1-carboxylate

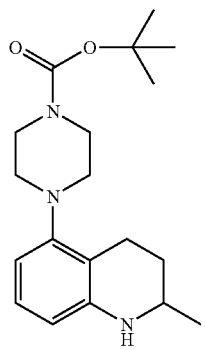

To a cold (0° C.) and stirred mixture of the tert-butyl 4-(2-methylquinolin-5-yl)piperazine-1-carboxylate prepared in example 6 (4.29 g, 13.1 mmol) and NiCl₂.6H₂O (0.78 g, 3.3 mmol) in MeOH (250 mL) was added portionwise NaBH₄ (3.96 g, 104.8 mmol) and then stirring was continued for 3 h. NaBH₄ was added when necessary. The solvent was evaporated in vacuo, the residue was treated with water and then extracted with CH₂Cl₂. After drying over MgSO₄, the solvent was evaporated in vacuo and the residue was purified by column chromatography (eluent CH₂Cl₂) to afford title compound (2.8 g, 51%). $R_f$=0.85 (CH₂Cl₂-MeOH 19:1).

Example 8

Preparation of tert-butyl 4-[2-methyl-1-(β-naphthyl-sulfonyl)quinolin-5-yl]piperazine-1-carboxylate

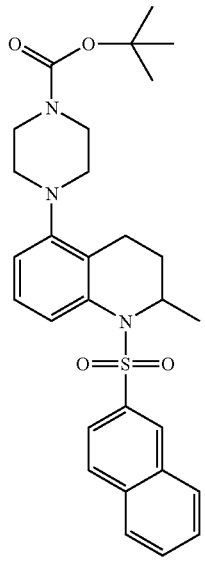

2-Naphthalenesulfonyl chloride (0.33 g, 1.45 mmol) was added to a solution of the tert-butyl 4-(1,2,3,4-tetrahydro-2-methylquinolin-5-yl)piperazine-1-carboxylate prepared in example 7 (0.4 g, 1.2 mmol), in pyridine (3 mL). The resulting mixture was heated under reflux for 3 h. The solvent was evaporated in vacuo and the residue was purified by column chromatography (using $CH_2Cl_2$ eluent). Yield: 0.26 g (41.2%). $R_f$=0.7 ($CH_2Cl_2$-acetone 98:2).

Example 9

Synthesis of 1,2,3,4-tetrahydro-2-methyl-5-(piperazin-1-yl)-1-(β-naphthylsulfonyl)quinoline trifluoroacetate (Compound 4)

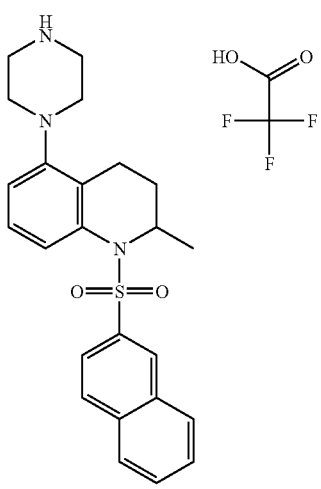

The compound prepared in example 8 (260 mg, 0.62 mmol) was dissolved in a mixture of 1 mL TFA and 4 mL $CH_2Cl_2$ and stirred for 30 min. The solvent was evaporated and the crude product was purified by a short silica gel column (using $CH_2Cl_2$-MeOH 98:2 as eluent). Yield: 180 mg (85.6%) $R_f$=0.38 ($CH_2Cl_2$-MeOH 9:1).

$^1$H NMR (CDCl$_3$): 0.94 (m, 1H, C$_4$—H), 1.06 (m, 1H, C$_3$—H), 1.27 (d, J=6.3 Hz, 3H, CH$_3$), 1.94 (m, 1H, C$_3$—H), 2.37 (m, 1H, C$_4$—H), 2.63 (br, 2H, C$_{2'}$—H and C$_{6'}$—H), 2.76 (br, 2H, C$_{2'}$—H and C$_{6'}$—H), 2.99 (br, 2H, C$_{3'}$—H and C$_{5'}$—H), 3.11 (br, 2H, C$_{3'}$—H and C$_{5'}$—H), 4.29 (m, 1H, C$_2$—H), 6.93 (d, J=8.0 Hz, 1H, C$_6$—H), 7.27 (t, J=8.0 Hz, 1H, C$_7$—H), 7.31 (dd, J=8.7 and 1.5 Hz, 1H, C$_{3''}$—H), 7.34 (d, J=8.0 Hz, 1H, C$_8$—H), 7.63 (t, J=7.5 Hz, 1H, C$_{7''}$-H), 7.69 (t, J=7.5 Hz, 1H, C$_{6''}$—H), 7.98 (d, J=8.9 Hz, 1H, C$_{4''}$—H), 8.00 (d, J=8.9 Hz, 1H, C$_{5''}$—H), 8.02 (d, J=8.3 Hz, 1H, C$_{8''}$—H), 8.11 (br s, C$_{1''}$—H), 8.92 (br s, 2H, NH$_2^+$).

$^{13}$C NMR (CDCl$_3$): 20.69 (C-4), 23.15 (CH$_3$), 31.83 (C-3), 43.15 (C-3' and C-5'), 48.50 (C-2' and C-6'), 53.24 (C-2), 116.33 (C-6), 122.26 (C-3''), 123.50 (C-8), 126.83 (C-7), 127.82 (C-7''), 127.95 (C-5''), 128.10 (C-1''), 129.17 (C-6''), 129.23 (C-4''), 129.38 (C-8''), 130.20 (C-4a), 131.61 (C-8a''), 134.42 (C-4a''), 135.04 (C-2''), 136.08 ((C-8a), 149.23 (C-5).

Example 10

Preparation of tert-butyl 4-[2-methyl-1-α-naphthyl-sulfonyl)quinolin-5-yl]piperazine-1-carboxylate

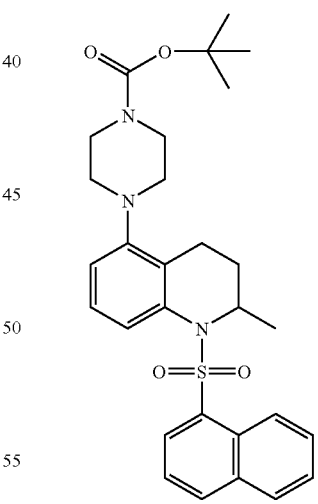

1-Naphthalenesulfonyl chloride (0.33 g, 1.45 mmol) was added to a solution of the tert-butyl 4-(1,2,3,4-tetrahydro-2-methylquinolin-5-yl)piperazine-1-carboxylate prepared in example 7 (0.4 g, 1.2 mmol), in pyridine (3 mL). The resulting mixture was heated under reflux for 30 h. The solvent was evaporated in vacuo and the residue was purified by column

Example 11

Synthesis of 1,2,3,4-tetrahydro-2-methyl-5-(piperazin-1-yl)-1-α-naphthylsulfonyl)quinoline trifluoroacetate (Compound 3)

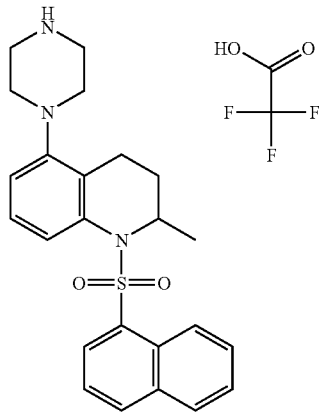

The tert-butyl 4-[2-methyl-1-(α-naphthylsulfonyl)quinolin-5-yl]piperazine-1-carboxylate prepared in example 10 (260 mg, 0.62 mmol) was dissolved in a mixture of 1 mL TFA and 4 mL $CH_2Cl_2$ and stirred for 30 min. The solvent was evaporated and the crude product was purified by a short silica gel column (using $CH_2Cl_2$-MeOH 98:2 eluent). Yield: 190 mg (97%) $R_f$=0.38 ($CH_2Cl_2$-MeOH 9:1).

$^1$H NMR ($CDCl_3$): 0.61 (m, 1H, $C_4$—H), 1.01 (m, 1H, $C_3$—H), 1.26 (d, J=6.5 Hz, 3H, $CH_3$), 1.84 (m, 1H, $C_3$—H), 2.23 (m, 1H, $C_4$—H), 2.36 (br, 2H, $C_{2'}$—H and $C_{6'}$—H), 2.60 (br, 2H, $C_{2'}$—H and $C_{6'}$—H), 2.98 (br, 2H, $C_{3'}$—H and $C_{5'}$—H), 3.08 (br, 2H, $C_{3'}$—H and $C_{5'}$—H), 4.17 (m, 1H, $C_2$—H), 6.91 (d, J=7.5 Hz, 1H, $C_6$—H), 7.14 (t, J=7.5 Hz, 1H, $C_{7''}$—H), 7.29 (m, 1H, $C_7$—H), 7.31 (m, 1H, $C_8$—H), 7.46 (t, J=7.5 Hz, 1H, $C_{6''}$—H), 7.63 (d, J=8.7 Hz, 1H, $C_{8''}$—H), 7.67 (t, J=8.0 Hz, 1H, $C_{3''}$—H), 7.98 (d, J=8.2 Hz, 1H, $C_{5''}$—H), 8.22 (d, J=7.5 Hz, 1H, $C_{2''}$—H), 8.24 (d, J=8.3 Hz, 1H, $C_{4''}$—H), 8.92 (br s, 2H, $NH_2^+$).

$^{13}$C NMR ($CDCl_3$): 20.39 (C-4), 22.94 ($CH_3$), 31.87 (C-3), 43.12 (C-3' and C-5'), 48.46 (C-2' and C-6'), 52.69 (C-2), 116.58 (C-6), 123.95 (C-8), 124.40 (C-8), 124.84 (C-3"), 126.68 (C-7"), 126.78 (C-7), 127.15 (C-7"), 128.05 (C-8a"), 128.69 (C-5"), 130.17 (C-2"), 130.84 (C-8a"), 133.93 (C-4a"), 134.65 (C-4"), 135.72 (C-8a), 149.02 (C-5).

Example 12

Synthesis of 1,2,3,4-tetrahydro-2-methyl-5-(piperazin-1-yl)-1-(benzenesulfonyl)quinoline trifluoroacetate (Compound 5)

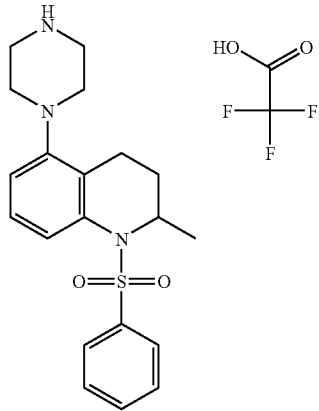

Benzenesulfonyl chloride (0.26 g, 1.45 mmol) was added to a solution of the tert-butyl 4-(1,2,3,4-tetrahydro-2-methylquinolin-5-yl)piperazine-1-carboxylate prepared in example 7 (0.4 g, 1.2 mmol), in pyridine (3 mL). The resulting mixture was heated at 80° C. for 1.5 h. The solvent was evaporated in vacuo and the residue was purified by a short column (using $CH_2Cl_2$ as eluent), $R_f$=0.64 ($CH_2Cl_2$-acetone 1%). The product was decarboxylated in a mixture of 1 mL TFA and 4 mL $CH_2Cl_2$ by stirring for 30 min. After evaporating the solvent, the crude product was purified by a short silica gel column (using $CH_2Cl_2$-MeOH 98:2 as eluent). Yield: 0.25 g (40.0%). $R_f$=0.35 ($CH_2Cl_2$-MeOH (9:1).

$^1$H-NMR ($DMSOd_6$): 0.98 (m, 1H, $C_4''$H), 1.06 (m, 1H, $C_3$—H), 1.24 (d, J=6.3 Hz, 3H, $CH_3$), 1.97 (m, 1H, $C_3$—H), 2.46 (M, 1H, $C_4$—H), 2.80 (m, 2H, $C_{2'}$—H and $C_{6'}$—H), 2.86 (m, 2H, $C_{2'}$—H and $C_{6'}$—H), 3.14 (m, 2H, $C_{3'}$—H and $C_{5'}$—H), 3.20 (M, 2H, $C_{3'}$—H and $C_{5'}$—H), 4.20 (m, 1H, $C_2$—H), 6.93 (d, J=7.8 Hz, $C_6$—H), 7.24 (m, 1H, $C_7$—H), 7.27 (m, 1H, $C_8$—H), 7.36 (d, J=7.8 Hz, 2H, $C_{2''}$—H and $C_{6''}$—H), 7.47 (t, J=7.8 Hz, 2H, $C_{3''}$—H and $C_{5''}$—H), 7.63 (t, J=7.4 Hz, 1H, $C_{4''}$—H), 8.99 (br. s, 2H, $NH_2$).

$^{13}$C-NMR ($DMSOd_6$): 20.65 (C-4), 23.22 ($CH_3$), 31.87 (C-3), 43.24 (C-3' and C-5'), 48.61 (C-2' and C-6'), 53.23 (C-2), 116.37 (C-6), 123.53 (C-8), 126.79 (C-7), 129.26 (C-3" and C-5"), 130.30 (C-4a), 133.31 (C-4"), 135.99 (C-8a), 137.83 (C-1"), 149.23 (C-5).

Example 13

Synthesis of 1,2,3,4-tetrahydro-2-methyl-5-(piperazin-1-yl)-1-(3-nitrophenylsulfonyl)quinoline trifluoroacetate (Compound 6)

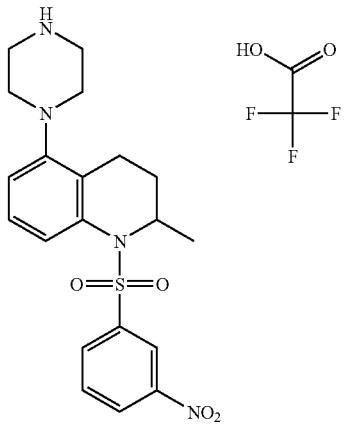

3-Nitrobenzenesulfonyl chloride (0.12 g, 1.54 mmol) was added to a solution of the tert-butyl 4-(1,2,3,4-tetrahydro-2-methylquinolin-5-yl)piperazine-1-carboxylate prepared in example 7 (0.15 g, 0.45 mmol), in pyridine (3 mL). The resulting mixture was heated at 100° C. for 40 h. The solvent was evaporated in vacuo and the residue was purified by a short column (using $CH_2Cl_2$ as eluent) $R_f$=0.57 ($CH_2Cl_2$-acetone 1%). The product was decarboxylated in a mixture of 1 mL TFA and 4 mL $CH_2Cl_2$ by stirring for 30 min. After evaporating the solvent, the crude product was purified by a short silica gel column (using $CH_2Cl_2$-MeOH 98:2 as eluent). Yield: 137 mg (55%). $R_f$=0.22 ($CH_2Cl_2$-MeOH 9:1).

$^1$H-NMR (DMSOd$_6$): 0.93 (m, 1H, C$_4$–H), 1.07 (m, 1H, C$_3$—H), 1.28 (d, J=6.3 Hz, 3H, CH$_3$), 2.02 (m, 1H, C$_3$—H), 2.48 (M, 1H, C$_4$—H), 2.79 (m, 4H, C$_{2'}$—H and C$_{6'}$—H), 3.10 (m, 2H, C$_{3'}$—H and C$_{5'}$—H), 3.19 (M, 2H, C$_{3'}$—H and C$_{5'}$—H), 4.19 (m, 1H, C$_2$—H), 6.99 (d, J=6.3 Hz, C$_6$—H), 7.31 (m, 2H, C$_7$—H and C$_8$—H), 7.81 (m, 2H, C$_{2''}$—H and C$_{5''}$—H), 7.86 (d, J=7.8 Hz, 1H, C$_{6''}$—H), 8.46 (dd, J=8.0 and 1.0 Hz, 1H, C$_{4''}$—H), 8.90 (br. s, 2H, NH$_2$).

$^{13}$C-NMR (DMSOd$_6$): 21.16 (C-4), 23.41 (CH$_3$), 32.25 (C-3), 43.28 (C-3' and C-5'), 48.48 (C-2' and C-6'), 54.11 (C-2), 116.79 (C-6), 121.31 (C-2''), 123.62 (C-8), 127.18 (C-7), 127.96 (C-4''), 130.53 (C-4a), 131.48 (C-5''), 132.69 (C-6''), 135.48 (C-8a), 138.83 (C-1''), 147.74 (C-3''), 149.47 (C-5).

Example 14

Synthesis of 1,2,3,4-tetrahydro-2-methyl-5-(piperazin-1-yl)-1-(4-methyl benzenesulfonyl)-quinoline trifluoroacetate (Compound 2)

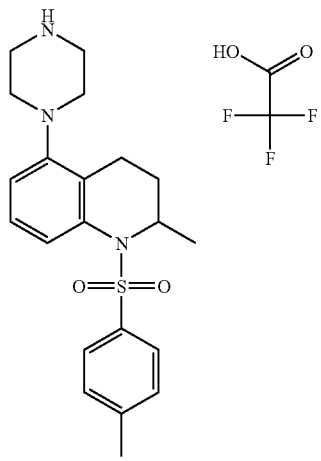

4-Methylbenzenesulfonyl chloride (276 mg, 1.45 mmol) was added to a solution of the tert-butyl 4-(1,2,3,4-tetrahydro-2-methylquinolin-5-yl)piperazine-1-carboxylate prepared in example 7 (0.4 g, 1.21 mmol), in pyridine (3 mL). The resulting mixture was heated at 100° C. for 2 h. The solvent was evaporated in vacuo and the residue was purified by a short column (using CH$_2$Cl$_2$ as eluent), R$_f$=0.78 (CH$_2$Cl$_2$-acetone 1%). The product was decarboxylated in a mixture of 1 mL TFA and 4 mL CH$_2$Cl$_2$ by stirring for 30 min. After evaporating the solvent, the crude product was purified by a short silica gel column (using CH$_2$Cl$_2$-MeOH 98:2 as eluent). Yield: 400 mg (63%). R$_f$=0.08 (CH$_2$Cl$_2$-MeOH 9.5: 0.5).

$^1$H NMR (CDCl$_3$): 1.08 (m, 2H, C$_3$—H), 1.23 (d, J=6.3 Hz, 3H, CH$_3$), 1.95 (m, 1H, C$_3$—H), 2.33 (s, 3H, CH$_3$), 2.46 (m, 1H, C$_4$—H), 2.80 (br, 2H, C$_{2'}$—H and C$_{6'}$—H), 2.86 (br, 2H, C$_{2'}$—H and C$_{6'}$—H), 3.15 (br, 2H, C$_{3'}$—H and C$_{5'}$—H), 3.21 (br, 2H, C$_{3'}$—H and C$_{5'}$—H), 4.20 (m, 1H, C$_2$—H), 6.92 (d, J=7.5 Hz, 1H, C$_6$—H), 7.23 (m, 1H, C$_8$—H), 7.26 (m, 5H, C$_7$—H, C$_{2''}$—H, C$_{3''}$—H, C$_{5''}$—H, C$_{6''}$—H), 8.96 (br s, 2H, NH$_2^+$).

$^{13}$C NMR (CDCl$_3$): 20.67 (C-4), 21.09 (CH$_3$), 23.09 (CH$_3$), 31.69 (C-3), 43.26 (C-3' and C-5'), 48.59 (C-2' and C-6'), 53.05 (C-2), 116.19 (C-6), 123.41 (C-8), 126.68 (C-7), 126.85 (C-2'' and C-6''), 129.61 (C-3'' and C-5''), 130.11 (C-4a), 135.12 (C-1''), 136.08 (C-8a), 143.71 (C-4''), 149.20 (C-5).

Example 15

Synthesis of 1,2,3,4-tetrahydro-2-methyl-5-(4-methylpiperazin-1-yl)-1-(4-methyl benzene-sulfonyl) quinoline trifluoroacetate (Compound 1)

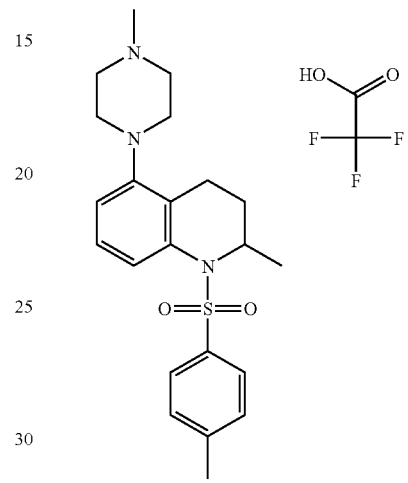

0.26 g (0.52 mmol) of 1,2,3,4-tetrahydro-2-methyl-5-(piperazin -1-yl)-1-(4-methylbenzenesulfonyl)quinoline prepared in example 14 and 67 mg (1.56 mmol, 45%) NaH was dissolved in 2 mL DMF at 0° C. After stirring 1 h at 0° C., the mixture was cooled to −78° C. and MeI was added (32 µL, 0.52 mmol). The reaction mixture was stirred over 1 night at room temperature After evaporating the solvent, the residue was dissolved in 15 mL water and extracted with EtOAc. The crude product was purified by column chromatography (eluent: CH$_2$Cl$_2$-MeOH 0.5%). Yield: 82 mg (38%) R$_f$=0.65 (CH$_2$Cl$_2$-MeOH 9:1).

$^1$H NMR (DMSO-d$_6$): 0.89 (m, 1H, C$_4$—H), 1.00 (m, 1H, C$_3$—H), 1.24 (d, J=6.5 Hz, 3H, CH$_3$), 1.96 (m, 1H, C$_3$—H), 2.22 (s, 3H, N—CH$_3$), 2.32 (s, 3H, CH$_3$), 2.39 (m, 1H, C$_4$—H), 2.4 (br, 4H, C$_{2'}$—H and C$_{6'}$—H), 2.63 (br s, 4H, C$_{3'}$—H and C$_{5'}$—H), 4.14 (m, 1H, C$_2$—H), 6.88 (dd, J=6.5 and 2.5 Hz, 1H, C$_6$—H), 7.18 (m, 2H, C$_7$—H and C$_8$—H), 7.20 (m, 2H, C$_{2''}$—H and C$_{6''}$—H), 7.25 (d, J=8.1, 2H, C$_{3''}$—H and C$_{5''}$—H).

$^{13}$C NMR (DMSO-d$_6$): 21.05 (CH$_3$), 21.17 (C-4), 23.57 (CH$_3$), 32.30 (C-3), 45.64 (CH$_3$), 51.27 (C-2' and C-6'), 53.44 (C-2), 54.84 (C-3' and C-5'), 115.92 (C-6), 122.91 (C-8), 126.51 (C-7), 126.86 (C-2'' and C-6''), 129.56 (C-3'' and C-5''), 130.58 (C-4a), 134.86 (C-1''), 135.91 (C-8a), 143.60 (C-4''), 150.10 (C-5).

In the following methods for determining the pharmacological activity of the substituted tetrahydro-quinoline-sulfonamide compounds are described.

Pharmacological Methods:

I) Binding to Serotonin Receptor 5-HT$_6$

Cell membranes of HEK-293 cells expressing the 5HT$_6$-human recombinant receptor were supplied by Receptor Biology. In said membranes the receptor concentration is 2.18 pmol/mg protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipsychotic Agents to 5-Hydroxytryptamine-6 and Hydroxytryptamine-7 Receptors. The Journal of Pharmacology and Experimental Therapeutics, 1994, 268, 1403] with the following slight changes. The respective part of the literature description is hereby incorporated by reference and forms part of the disclosure.

The commercial membrane is diluted (1:40 dilution) with the binding buffer: 50 mM Tris-HCl, 10 mM MgCl$_2$, 0.5 mM EDTA (pH 7.4). The radioligand used is [$^3$H]-LSD at a concentration of 2.7 nM with a final volume of 200 µl. Incubation is initiated by adding 100 µl of membrane suspension, (≈22.9 µg membrane protein), and is prolonged for 60 minutes at a temperature of 37° C. The incubation is ended by fast filtration in a Brandel Cell Harvester through fiber glass filters made by Schleicher & Schuell GF 3362 pretreated with a solution of polyethylenimine at 0.5%. The filters are washed three times with three milliliters of buffer Tris-HCl 50 mM pH 7.4. The filters are transferred to flasks and 5 ml of Ecoscint H liquid scintillation cocktail are added to each flask. The flasks are allowed to reach equilibrium for several hours before counting with a Wallac Winspectral 1414 scintillation counter. Non-specific binding is determined in the presence of 100 µM of serotonin. Tests were made in triplicate. The inhibition constants (K$_i$, nM) were calculated by non-linear regression analysis using the program EBDA/LIGAND [Munson and Rodbard, *Analytical Biochemistry*, 1980, 107, 220]., the respective part of which is hereby incorporated by reference and forms part of the disclosure.

The following table shows the binding results for some of the compounds object of the present invention.

| Compound | % Inhibition 10$^{-7}$ M | K$_i$ (nM) |
|---|---|---|
| 1 | | |
| 2 | | |
| 3 | 85.8 | 31.4 ± 0.8 |
| 4 | | |
| 5 | | |
| 6 | | |

Pharmaceutical Formulation

Example of formula per tablet:

| | |
|---|---|
| Compound 3 | 5 mg |
| Lactose | 60 mg |
| Crystalline cellulose | 25 mg |
| Povidone K 90 | 5 mg |
| Pregelatinised starch | 3 mg |
| Colloidal silica dioxide | 1 mg |
| Magnesium stereate | 1 mg |
| Total weight per tablet | 100 mg |

The invention claimed is:

1. A tetrahydro-quinoline-sulfonamide of general formula (I)

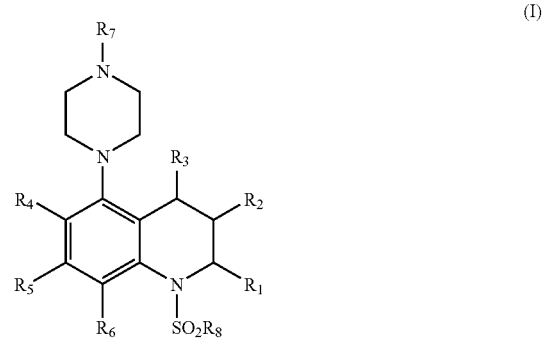

wherein

R$_1$, R$_2$ and R$_3$, independent from one another, each represent a hydrogen atom; or a linear or branched, saturated or unsaturated C$_{1-6}$ aliphatic radical which may be substituted with 1, 2 or 3 substituent(s) independently selected from the group consisting of F, Cl, Br, —OH, —O—CH$_3$, —O—C$_2$H$_5$, —CN with the proviso that at least one of R$_1$, R$_2$ and R$_3$ is a C$_{1-6}$ alkyl group optionally substituted with 1, 2 or 3 substituent(s) as defined above;

R$_4$, R$_5$ and R$_6$, independent from one another, each represent a hydrogen atom or a chlorine atom;

R$_7$ represents a hydrogen atom; or a linear or branched, saturated or unsaturated C$_{1-6}$ aliphatic radical which may be substituted with 1, 2 or 3 substituent(s) independently selected from the group consisting of F, —OH, —O—CH$_3$ and —O—C$_2$H$_5$; and R$_8$ represents a 6- to 10-membered aryl radical which may be substituted with 1, 2 or 3 substituent(s) independently selected from the group consisting of —CH$_3$, —C$_2$H$_5$, Cl, Br, —OH, —NH$_2$, —SH, —O—CH$_3$, —O—C$_2$H$_5$, —NO$_2$, —CN, —NH—CH$_3$ and —S—CH$_3$;

optionally in form of one of its stereoisomers, a racemate or in form of a mixture of at least two of its stereoisomers, in any mixing ratio, or a physiologically acceptable salt, thereof.

2. A tetrahydro-quinoline-sulfonamide of general formula (I) according to claim 1 selected from the following group:

[1] 1,2,3,4-Tetrahydro-2-methyl-5-(4-methylpiperazin-1-yl)-1-(4-methylbenzene-sulfonyl)quinoline trifluoroacetate;

[2] 1,2,3,4-Tetrahydro-2-methyl-5-(piperazin-1-yl)-1-(4-methylbenzenesulfonyl)-quinoline trifluoroacetate;

[3] 1,2,3,4-Tetrahydro-2-methyl-5-(piperazin-1-yl)-1-(α-naphthylsulfonyl)quinoline trifluoroacetate;

[4] 1,2,3,4-Tetrahydro-2-methyl-5-(piperazin-1-yl)-1-(β-naphthylsulfonyl)quinoline trifluoroacetate;

[5] 1,2,3,4-Tetrahydro-2-methyl-5-(piperazin-1-yl)-1-(benzenesulfonyl)quinoline trifluoroacetate; and

[6] 1,2,3,4-Tetrahydro-2-methyl-5-(piperazin-1-yl)-1-(3-nitrophenylsulfonyl)quinoline trifluoroacetate.

3. A method for producing a tetrahydro-quinoline-sulfonamide of general formula (I) that comprises reacting a compound of general formula (II)

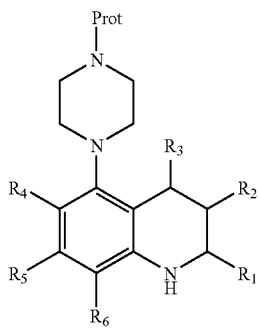
(II)

wherein Prot is an N-protecting group;
wherein $R_1$, $R_2$ and $R_3$, independent from one another, each represent a hydrogen atom; or a linear or branched, saturated or unsaturated $C_{1-6}$ aliphatic radical which may be substituted with 1, 2 or 3 substituent(s) independently selected from the group consisting of F, Cl, Br, —OH, —O—$CH_3$, —O—$C_2H_5$, —CN,
with the proviso that at least one of $R_1$, $R_2$ and $R_3$ is a $C_{1-6}$ alkyl group optionally substituted with 1, 2 or 3 substituent(s) as defined above; and
wherein $R_4$, $R_5$ and $R_6$, independent from one another, each represent a hydrogen atom or a chlorine atom;
with a sulfonyl derivative of general formula (III):

$R_8SO_2X$      (III)

wherein $R_8$ represents a 6- to 10-membered aryl radical which may be substituted with 1, 2 or 3 substituent(s) independently selected from the group consisting of —$CH_3$, —$C_2H_5$, Cl, Br, —OH, —$NH_2$, —SH, —O—$CH_3$, —O—$C_2H_5$, —$NO_2$, —CN, —NH—$CH_3$; and —S—$CH_3$; and X is a leaving group for producing the compound of general formula (IV):

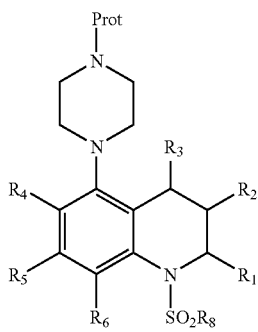
(IV)

wherein $R_1$, $R_2$, $R_3$, $R_4$, $R_5$, $R_6$ and $R_8$ have the meanings defined above, and Prot has the meanings defined above;
removing the N-protecting group for producing the compound of general formula (I) wherein $R_7$ represents a hydrogen atom; and
optionally reacting the compound of general formula (I) wherein $R_7$ represents a hydrogen atom with a compound of general formula (V):

R'X      (V)

wherein X is a leaving group and R' represents a linear or branched, saturated or unsaturated $C_{1-6}$ aliphatic radical which may be substituted with 1, 2 or 3 substituent(s) independently selected from the group consisting of F, —OH, —O—$CH_3$ and —O—$C_2H_5$;
for producing the compound of general formula (I) wherein $R_7$ represents a linear or branched, saturated or unsaturated $C_{1-6}$ aliphatic radical which may be substituted with 1, 2 or 3 substituent(s) independently selected from the group consisting of F, —OH, —O—$CH_3$ and —O—$C_2H_5$.

4. A method for producing a tetrahydro-quinoline-sulfonamide of general formula (I) wherein $R_7$ represents a linear or branched, saturated or unsaturated $C_{1-6}$ aliphatic radical which may be substituted with 1, 2 or 3 substituent(s) independently selected from the group consisting of F, —OH, —O—$CH_3$ and —O—$C_2H_5$, that comprises a compound of general formula (VI)

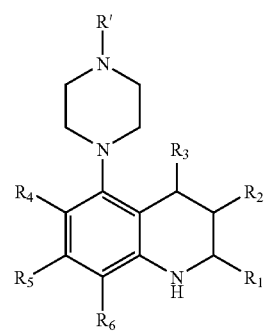
(VI)

wherein $R_1$, $R_2$ and $R_3$, independent from one another, each represent a hydrogen atom; or a linear or branched, saturated or unsaturated $C_{1-6}$ aliphatic radical which may be substituted with 1, 2 or 3 substituent(s) independently selected from the group consisting of F, Cl, Br, —OH, —O—$CH_3$, —O—$C_2H_5$, —CN,
with the proviso that at least one of $R_1$, $R_2$ and $R_3$ is a $C_{1-6}$ alkyl group optionally substituted with 1, 2 or 3 substituent(s) as defined above;
wherein $R_4$, $R_5$ and $R_6$, independent from one another, each represent a hydrogen atom or a chlorine atom; and
wherein R' is a linear or branched, saturated or unsaturated $C_{1-6}$ aliphatic radical which may be substituted with 1, 2 or 3 substituent(s) independently selected from the group consisting of F, —OH, —O—$CH_3$ and —O—$C_2H_5$;
with a sulfonyl derivative of general formula (III):

$R_8SO_2X$ (III)

wherein $R_8$ represents a 6- to 10-membered aryl radical which may be substituted with 1, 2 or 3 substituent(s) independently selected from the group consisting of —$CH_3$, —$C_2H_5$, Cl, Br, —OH, —$NH_2$, —SH, —O—$CH_3$, —O—$C_2H_5$, —$NO_2$, —CN, —NH—$CH_3$ and —S—$CH_3$, and X is a leaving group.

5. A medicament comprising at least one substituted tetrahydro-quinoline-sulfonamide according to claim 1 and optionally at least one physiologically acceptable auxiliary agent.

6. A method of treatment of a disorder that is at least partially mediated via 5-HT6 receptors comprising administering to a mammal at least one substituted tetrahydro-quinoline-sulfonamide according to claim 1, wherein the disorder is selected from the group consisting of depression; schizophrenia; obesity; and mild cognitive impairment.

7. The method of claim 6, wherein said disorder is depression.

8. The method of claim 6, wherein said disorder is schizophrenia.

9. The method of claim 6, wherein said disorder is obesity.

10. The method of claim 6, wherein said disorder is mild cognitive impairment.

* * * * *